(12) United States Patent
Coyle et al.

(10) Patent No.: US 8,283,642 B2
(45) Date of Patent: Oct. 9, 2012

(54) ION BEAM SAMPLE PREPARATION APPARATUS AND METHODS

(75) Inventors: Steven Thomas Coyle, Alameda, CA (US); John Andrew Hunt, Fremont, CA (US)

(73) Assignee: Gatan, Inc., Pleasanton, CA (US)

( * ) Notice: Subject to any disclaimer, the term of this patent is extended or adjusted under 35 U.S.C. 154(b) by 0 days.

(21) Appl. No.: 13/082,373

(22) Filed: Apr. 7, 2011

(65) Prior Publication Data

US 2012/0085939 A1     Apr. 12, 2012

Related U.S. Application Data

(60) Provisional application No. 61/322,870, filed on Apr. 11, 2010.

(51) Int. Cl.
  *G21K 5/10*   (2006.01)
  *H01J 37/08*  (2006.01)
  *H01J 37/30*  (2006.01)
  *H01J 37/31*  (2006.01)

(52) U.S. Cl. ............ 250/492.21; 250/492.3; 250/309

(58) Field of Classification Search ........... 250/309, 250/310, 397, 398, 492.2, 492.21, 492.3, 250/505.1
See application file for complete search history.

(56) References Cited

U.S. PATENT DOCUMENTS

| | | | |
|---|---|---|---|
| 4,272,682 A | 6/1981 | Swann | |
| 5,472,566 A | 12/1995 | Swann et al. | |
| 5,907,157 A | 5/1999 | Yoshioka et al. | |
| 5,922,179 A | 7/1999 | Mitro et al. | |
| 5,986,264 A | 11/1999 | Grunewald | |
| 6,406,589 B1 | 6/2002 | Yanagisawa | |
| 6,768,110 B2 | 7/2004 | Alani | |
| 6,784,427 B1 | 8/2004 | Grunewald et al. | |
| 6,914,244 B2 | 7/2005 | Alani | |
| 7,276,712 B2 * | 10/2007 | Ferrara | 250/492.21 |
| 7,351,986 B2 * | 4/2008 | Murrell | 250/492.21 |
| 7,354,500 B2 | 4/2008 | Yoshioka et al. | |
| 7,453,073 B2 * | 11/2008 | Yoshioka | 250/492.21 |
| 7,552,524 B2 * | 6/2009 | Ma et al. | 29/603.16 |
| 7,722,818 B2 * | 5/2010 | Hasegawa et al. | 422/502 |

(Continued)

FOREIGN PATENT DOCUMENTS

EP     1921434     5/2008

(Continued)

*Primary Examiner* — Bernard E Souw
(74) *Attorney, Agent, or Firm* — Theodore Heske, III

(57) ABSTRACT

Disclosed are embodiments of an ion beam sample preparation apparatus and methods for using the embodiments. The apparatus comprises a tilting ion beam irradiating means in a vacuum chamber that may direct ions toward a sample, a shield blocking a portion of the ions directed toward the sample, and a shield retention stage with shield retention means that replaceably and removably holds the shield in a position. The shield has datum features which abut complementary datum features on the shield retention stage when the shield is held in the shield retention stage. The shield has features which enable the durable adhering of the sample to the shield for processing the sample with the ion beam. The complementary datum features on both shield and shield retention stage enable accurate and repeatable positioning of the sample in the apparatus for sample processing and reprocessing. The tilting ion beam irradiating means may direct ions at the sample from more than one tilt angle. A rotating shield retention stage is also disclosed which works in concert with the tilting ion beam irradiating means to improve the flexibility and efficiency of the apparatus in preparing samples for microscopic observation.

26 Claims, 8 Drawing Sheets

U.S. PATENT DOCUMENTS

| | | | |
|---|---|---|---|
| 2004/0222082 A1* | 11/2004 | Gopalraja et al. | 204/192.3 |
| 2005/0081997 A1 | 4/2005 | Yoshioka et al. | |
| 2005/0118065 A1* | 6/2005 | Hasegawa et al. | 422/99 |
| 2005/0191409 A1* | 9/2005 | Murrell et al. | 427/8 |
| 2005/0232726 A1* | 10/2005 | Murrell | 414/217 |
| 2006/0113496 A1* | 6/2006 | Yoshioka | 250/492.21 |
| 2006/0255295 A1 | 11/2006 | Yoshioka et al. | |
| 2008/0067443 A1 | 3/2008 | Todoroki et al. | |
| 2012/0085923 A1* | 4/2012 | Coyle et al. | 250/453.11 |
| 2012/0085937 A1* | 4/2012 | Coyle et al. | 250/492.3 |
| 2012/0085938 A1* | 4/2012 | Coyle et al. | 250/492.3 |

FOREIGN PATENT DOCUMENTS

JP          2006 201002          8/2006

* cited by examiner

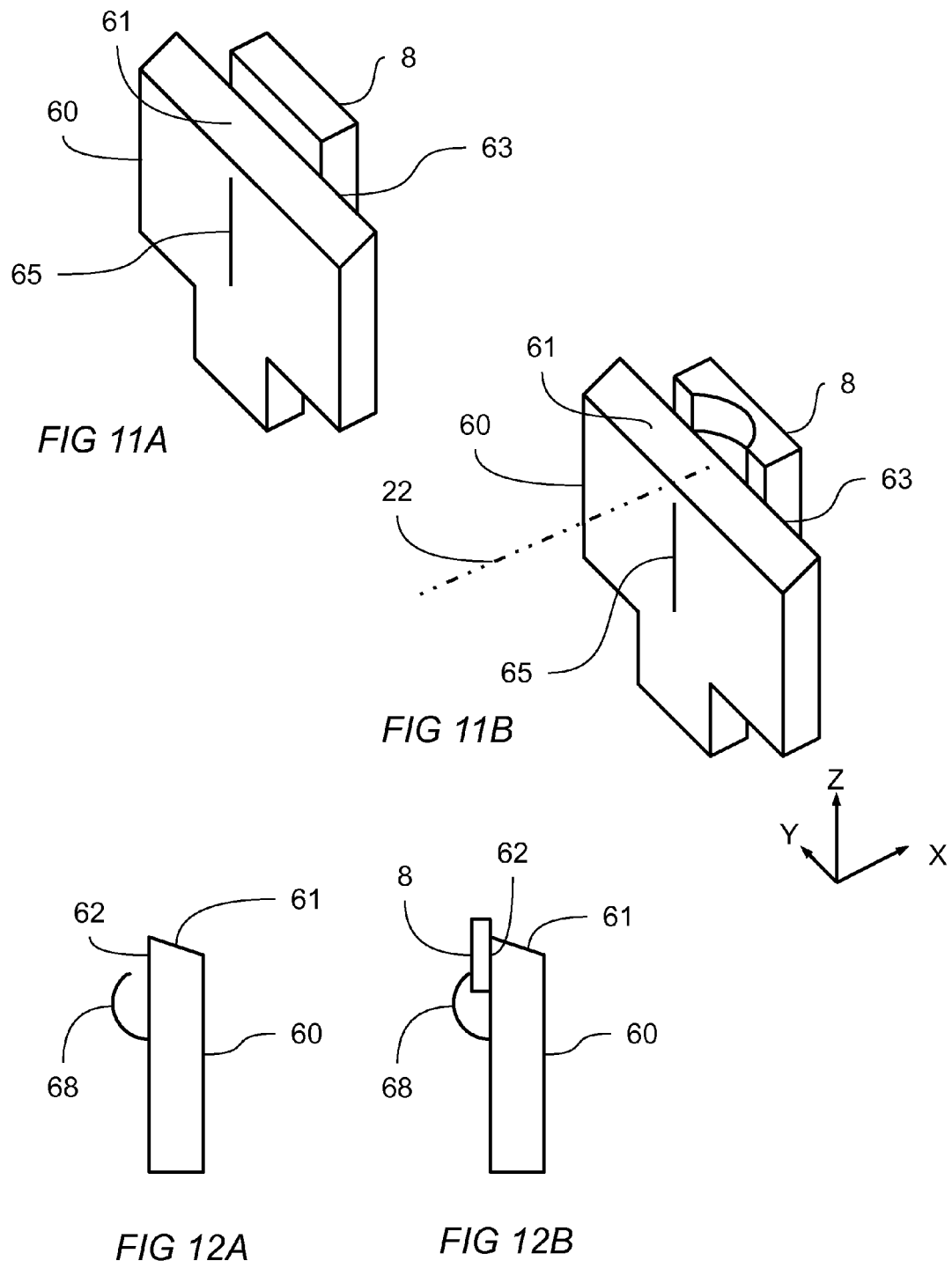

ION BEAM SAMPLE PREPARATION APPARATUS AND METHODS

CROSS REFERENCE TO RELATED APPLICATIONS

This non-provisional utility application claims the benefit of prior filed provisional Application No. 61/322,870 filed Apr. 11, 2010. Application No. 61/322,870 is incorporated herein by reference.

STATEMENT REGARDING FEDERALLY SPONSORED RESEARCH OR DEVELOPMENT

Not Applicable.

DESCRIPTION OF ATTACHED APPENDIX

Not Applicable.

BACKGROUND

The present disclosure relates to the use of one or more ion beams to prepare materials for microscopic observation or spectroscopic analysis. Microscopic observational techniques include, but are not limited to, optical microscopy, scanning electron microscopy (SEM), transmission electron microscopy (TEM), scanning transmission electron microscopy (STEM), reflection electron microscopy (REM). Spectroscopic analysis techniques include, but are not limited to, x-ray micro-analysis, reflection electron energy-loss spectroscopy (REELS), electron back-scattered diffraction (EBSD), x-ray photoelectron spectroscopy (XPS), and Auger electron spectroscopy (AES). Materials to be viewed under any microscopic technique may require processing to produce a sample suitable for microscopic examination.

Ion beam milling of a material can produce samples that are well suited for microscopic examination. An ion beam irradiating device may generate, accelerate, and direct a beam of ions toward a sample. The impact of ions on the sample sputters material away from the area of ion impact. Furthermore, the sample surface may be polished by the ion beam to a substantially smooth condition further enhancing observational properties of the sample. Regions of interest in the sample may be exposed and polished by the use of ion beams thus making a suitable observational sample from the material under investigation.

Broad Ion Beam Slope-Cutting (BIBSC), also known as cross section cutting using broad ion beam sources or cross section polishing using broad ion beam sources, is a rapid method for removing sample material to expose a smooth and substantially artifact-free cross-sectional surface for ultimate analysis by various microscopies and spectroscopies. A notable advantage of the BIBSC technique is high rates of surface preparation that can exceed tens or hundreds or thousands of square microns per hour, often over sample milling times of tens or hundreds of minutes.

Important considerations to users of the BIBSC technique include: reducing or minimizing the effort and time that the user is occupied in processing the sample; reducing or minimizing the number of steps where delicate samples are directly handled and at risk for damage, such as during mounting to sample holders for processing or analysis; reducing or minimizing the time and effort the user is occupied transferring the sample into the ultimate analysis equipment (imaging or spectroscopy), and aligning the coordinates of the prepared sample region to the ultimate analysis equipment prior to analysis; ensuring high quality and high probability of success in processing and imaging the sample; reducing or minimizing the time that the BIBSC ion milling equipment and sample mounting equipment are occupied for each sample; and ensuring high-quality microscopy observation of the sample during sample mounting and ultimate analysis by reducing the working distance required between the sample and the objective or probe-forming lens used for observation.

A sample that has been prepared in the ion beam may be evaluated by various methods to determine if the region of interest has been adequately exposed and prepared for observation. It may happen that the region of interest in the sample has not been adequately exposed or prepared. Embodiments of the present disclosure address this common situation. Embodiments of the present disclosure teach methods and apparatus for repeatably positioning a sample within an ion beam sample preparation apparatus thereby facilitating accurate processing and reprocessing of a sample. Further embodiments of the present disclosure teach methods and apparatus for preparing the sample using a tilting ion beam, making use of controlled ion beam tilt angle to expose regions of interest in the sample. Further embodiments of the present disclosure teach methods and apparatus for rotating the sample during preparation using a tilting ion beam, thereby achieving a more consistent and more desirable surface for later observation.

In consideration of the foregoing points, it is clear that embodiments of the present disclosure confer numerous advantages and are therefore highly desirable.

SUMMARY

The present disclosure is directed to ion beam sample preparation apparatus and methods for using the disclosed apparatus to prepare samples for later observation. The apparatus has features to quickly and repeatably retain and release both unprepared samples and prepared samples thereby facilitating preparation of samples in the ion beam apparatus and also facilitating the observation of the prepared samples in an observation apparatus. Features of the disclosure enable accurate and repeatable positioning of the sample both within the ion beam sample preparation apparatus and also within observation apparatus later used for observing prepared samples. Tilting ion beam features of the present disclosure allow additional flexibility in exposing regions of interest in the sample. Tilting ion beam features allow the sample to be prepared by the ion beam using more than one tilt angle of the ion beam. A previously prepared sample may be replaced in the apparatus and then prepared using a different tilt angle of the ion beam thereby exposing and preparing a different region of the sample. Further features of the disclosure teach methods and apparatus for rotating the sample during preparation using a tilting ion beam thereby achieving a more consistent and more desirable surface for later observation.

An embodiment according to the present disclosure of an apparatus for ion beam sample preparation comprises: an ion beam sample preparation apparatus comprising: a tilting ion beam irradiating means disposed in a vacuum chamber and directing an ion beam toward a shield, characterized in that said tilting ion beam irradiating means projects an ion beam along a central ion beam axis, the direction of said central ion beam axis having a tilt angle with respect to said shield; a tilt drive operably coupled to said tilting ion beam irradiating means and configured to move the direction of said central ion beam axis between at least two different tilt angles; a shield retention stage disposed in the vacuum chamber; said shield retention stage comprising: a first datum feature; a second datum feature; a shield retention means having at least a shield releasing position and a shield retaining position; the shield having at least a rigid planar portion, removably and replaceably held in said shield retention stage, said shield further comprising: a proximal sample surface configured to durably adhere the sample to the shield; a first shielding surface disposed in the path of the ion beam and positioned to shield a portion of the ion beam directed at the sample when said shield is held in the shield retaining position of the shield retention means; a third datum feature formed integrally with said shield, wherein said shield retention means in said shield retaining position urges said third datum feature to abut said first datum feature; and, a fourth datum feature formed integrally with said shield, wherein said shield retention means in said shield retaining position urges said fourth datum feature to abut said second datum feature.

In a related embodiment of the ion beam sample preparation apparatus, the shield retention stage further comprises a fifth datum feature, and the shield further comprises a sixth datum feature formed integrally with the shield, wherein the shield retention means in said shield retaining position urges said sixth datum feature to abut said fifth datum feature.

In a related embodiment of the ion beam sample preparation apparatus, the first shielding surface meets said proximal sample surface at an angle of less than about 90 degrees and more than about 80 degrees.

In a related embodiment of the ion beam sample preparation apparatus, the first shielding surface meets said proximal sample surface at an angle of less than about 87 degrees and more than about 83 degrees.

In a related embodiment of the ion beam sample preparation apparatus, the first shielding surface is made of non-magnetic material having low sputtering-yield.

In a related embodiment of the ion beam sample preparation apparatus, at least a portion of the first shielding surface is made of tantalum or titanium.

In a related embodiment of the ion beam sample preparation apparatus, the third datum feature is a datum surface, and at least a portion of said datum surface is coextensive with at least a portion of said proximal sample surface.

In a related embodiment of the ion beam sample preparation, the proximal sample surface has at least one recessed portion configured for the flowing of adhesive between the shield and the sample.

In a related embodiment of the ion beam sample preparation apparatus, the shield further comprises a sample clamping means coupled to the shield and configured to hold the sample against said proximal sample surface.

In a related embodiment of the ion beam sample preparation apparatus, the shield further comprises: a second shielding surface having a portion disposed in the path of a portion of the ion beam; a shield edge formed where the first shielding surface meets the proximal sample surface; and a visible alignment mark on the second shielding surface, configured such that the location of said visible alignment mark is in a predetermined relationship to the region where the ion beam impinges on said shield edge when said shield is held in the shield retaining position of the shield retention means.

In a related embodiment of the ion beam sample preparation apparatus, the shield is made of a cladding material joined to a core material such that a portion of the cladding material forms at least a portion of the first shielding surface, and a portion of the core material forms the third and fourth datum features of the shield. In a related embodiment, the cladding material is a non-magnetic material having low sputtering-yield.

Another embodiment of the present disclosure is directed to an apparatus for ion beam sample preparation which comprises: a tilting ion beam irradiating means disposed in a vacuum chamber and directing an ion beam toward a shield, characterized in that said tilting ion beam irradiating means projects an ion beam along a central ion beam axis, the direction of said central ion beam axis having a tilt angle with respect to said shield; a tilt drive operably coupled to said tilting ion beam irradiating means and configured to move the direction of said central ion beam axis between at least two different tilt angles; a rotating shield retention stage disposed in the vacuum chamber; said shield retention stage comprising: a first datum feature; a second datum feature; a shield retention means having at least a shield releasing position and a shield retaining position; a rotation axis located substantially in the plane of the first datum feature; a rotation drive for rotating the shield retention stage around the rotation axis; the shield having at least a rigid planar portion, removably and replaceably held in said shield retention stage, said shield further comprising: a third datum feature formed integrally with the shield, wherein said shield retention means in said shield retaining position urges said third datum feature to abut said first datum feature; a fourth datum feature formed integrally with the shield, wherein said shield retention means in said shield retaining position urges said fourth datum feature to abut said second datum feature; a first shielding surface disposed in the path of the ion beam and positioned to shield a portion of the ion beam directed at the sample when said shield is held in the shield retaining position of the shield retention means; a proximal sample surface configured to durably adhere the sample to the shield; a shield edge formed where the first shielding surface meets the proximal sample surface, characterized in that said shield edge is held substantially perpendicular to said rotation axis when said shield is held in the shield retaining position of the shield retention means.

In a related embodiment of the ion beam sample preparation apparatus, the apparatus is further characterized in that the tilting ion beam irradiating means and tilt drive are adapted to provide at least two different tilt angles in which the central ion beam axis is substantially perpendicular to said shield edge.

In a related embodiment of the ion beam sample preparation apparatus, the apparatus is further characterized in that the tilting ion beam irradiating means and tilt drive are adapted to provide at least two different tilt angles in which the central ion beam axis substantially intersects said rotation axis.

BRIEF DESCRIPTION OF THE DRAWINGS

These and other features, aspects, and advantages of the present invention will become better understood with regard to the following description, appended claims, and accompanying drawings where:

FIGS. 11A and 11B show perspective views of a shield with a durably adhered sample, both before (FIG. 11A) and after (FIG. 11B) preparation in an ion beam sample preparation apparatus according to the present disclosure.

FIGS. 12A and 12B show an embodiment of a shield with integrated sample clamping means according to an embodiment of the present disclosure.

LIST OF REFERENCE NUMBERS APPEARING IN THE FIGURES

Figure 1:
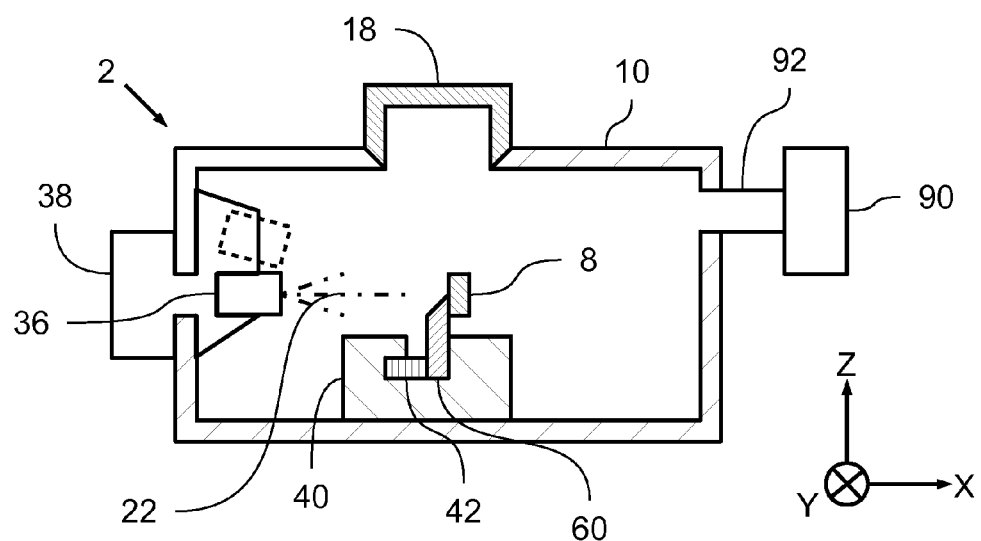
FIG. 1 shows a schematic cross sectional view of an ion beam sample preparation apparatus according to an embodiment of the present disclosure featuring a tilting ion beam irradiating means. The tilting irradiating ion beam means is shown with the tilting ion beam irradiating means at a first tilt angle.

2—ion beam sample preparation thermal management apparatus
8—sample
10—vacuum chamber
18—chamber cover
20—ion beam irradiating means
22—central ion beam axis
36—tilting ion beam irradiating means
38—tilt drive
40—shield retention stage
42—shield retention means
42a—shield retention means first member
42b—shield retention means second member
46—shield retaining position
48—shield releasing position
50—rotating shield retention stage
52—rotation drive
54—rotation axis
56—vacuum seal
60—shield
61—shielding surface
61a, 61b, etc.—first shielding surface, second shielding surface, etc.
62—proximal sample surface
63—shield edge
64—recessed portion
65—visible alignment mark
66—core material
67—cladding material
68—sample clamping means
70a, 70b, 70c, 70d, 70e, 70f—first datum feature, second datum feature, third datum feature, fourth datum feature, fifth datum feature, sixth datum feature.
72—datum surface
90—vacuum pump means
92—pumping manifold

DESCRIPTION

The Broad Ion Beam Slope-Cutting (BIBSC) sample preparation procedure can be described as a series of process steps, p1-p5:
  p1) Aligning the desired region of the sample to be processed to a usable portion of an ion shield;
  p2) Aligning the sample and shield in the BIBSC ion-milling system such that the desired region of the sample can be processed by the ion beam or beams;
  p3) Evacuating the ion-milling system to vacuum levels appropriate for ion beam milling;
  p4) Performing the ion-milling operation or operations, sometimes using a process monitoring step such as in situ light-microscopy imaging to verify sufficient cut depth and quality of the cross section;
  p5) Venting of the BIBSC ion-milling equipment and removal of the sample from the equipment.

The analysis of prepared BIBSC sample can be described as a series of process steps, p6-p9:
  p6) Introduction of the sample to the ultimate analysis microscope and initializing the microscope so that analysis can commence;
  p7) Finding the location of the prepared cross-sectional surface by adjusting any number of the microscope's translation stages, tilt stages, and rotation stages so that the desired area can be imaged;
  p8) Performing the desired microscopic or spectroscopic analyses;
  p9) Removing the sample from the microscope;
  p10) After analyzing the sample, a decision may be made to reprocess the sample to change the cut depth, position, or angle—traditionally requiring a repeat of p1-p9.

Embodiments of the present disclosure uniquely permit certain efficiencies and capabilities in the processing and subsequent observation and analysis of BIBSC produced samples. Beneficial features, functions, and aspects of the present disclosure include, but are not limited to:
  1. Datum features on the shield, shield retention device in the sample-to-shield mounting apparatus, shield retention device in the BIBSC ion-mill, shield retention device in the ultimate analysis equipment allow significant time efficiencies in processing steps p1, p2 and p7;

2. The integral nature of the sample durably adhered to the shield, and to a lesser extent with the sample merely clamped to the shield, allows greater certainty in ensuring alignment of the shield to the sample remains consistent during p4 even over long time-scales and changes in temperature, whereas quality of the cross section cutting process is reduced if this precision alignment is not maintained;

3. The integral nature of the sample durably adhered to the shield in processing step p1 eliminates the requirement for expensive and sizable fixturing apparatus to maintain their spatial relationship together throughout the milling operation, and enables multiple samples to be prepared in advance of milling without multiple fixturing apparatus;

4. The integral nature of the sample durably adhered or clamped to the shield eliminates the requirement for dismounting the sample from the shield prior to observation in a microscope, even in cases where the smallest working distances between imaging objective and sample are employed. This permits reduction of both time and risk of damage to the sample during sample remounting in processing step p6;

5. In the case where reprocessing the sample as in step p10 is performed, the integral nature of the sample durably adhered or clamped to the shield can eliminate the need for steps p1 and p2 entirely, which significantly reduces processing time and risk of damage to the sample during sample remounting; and, 6. In the case where reprocessing the sample as in step p10 is performed, the integral nature of the sample durably adhered or clamped to the shield allows different cross-sectional planes to be cut very close to the originally cut cross-sectional plane by varying the angle of ion beam impinging on the sample and shield.

Turning now to FIG. 1, illustrated is a schematic cross sectional view of an embodiment of an ion beam sample preparation apparatus 2 according to the present disclosure. The embodiment of FIG. 1 is shown comprising: a vacuum chamber 10 in which a sample 8 is prepared; chamber cover 18 which seals vacuum chamber 10 from the outside atmosphere; vacuum pump means 90 and pumping manifold 92, which together bring vacuum chamber 10 to vacuum levels appropriate for ion beam milling; tilting ion beam irradiating means 36 and tilt drive 38, which creates and directs an ion beam having a central ion beam axis 22 toward sample 8; a shield 60, which shields at least a portion of sample 8 from at least a portion of the ion beam; a shield retention stage 40, which holds and accurately positions shield 60 with respect to the direction and extent of the ion beam; a shield retention means 42, which both retains shield 60 in shield retention stage 40, and also urges shield 60 to remain in a position whereby the ion beam may prepare sample 8.

With continuing reference to FIG. 1, the ion beam preferably comprises noble gas ions. Elements used for the ion beam may include but are not limited to: Argon, Xenon, and Krypton. The ion beam may also comprise a mixture of ions and neutrals. Shield retention stage 40 is disposed in vacuum chamber 10 in a predetermined position and orientation with respect to central ion beam axis 22. Tilting ion beam irradiating means 36 and tilt drive 38 enable the ion beam to prepare the sample by directing central ion beam axis 22 toward sample 8 from more than one tilt angle with respect to shield 60. FIG. 1 shows tilting ion beam irradiating means 36 operating at a first tilt angle.

Figure 2:
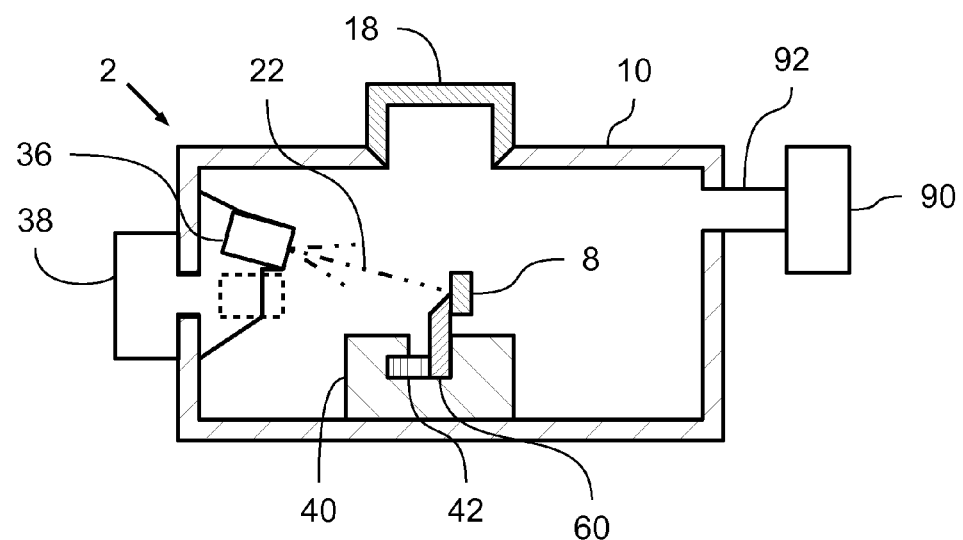
FIG. 2 shows a schematic cross sectional view of the apparatus of FIG. 1 at a second tilt angle.

FIG. 2 shows the same apparatus as in FIG. 1. However, the apparatus of FIG. 2 is shown after the tilt drive 38 has operated to move tilting ion beam irradiating means 36 to a different tilt angle than in FIG. 1. After the sample has been prepared by the ion beam in the vacuum chamber, chamber cover 18 may be opened; then the shield and sample may be removed for observation in a microscope.

The tilting ion beam irradiating means and drive shown in the embodiments of FIG. 1 and FIG. 2 give the user additional flexibility in preparing a sample for later observation. In particular, a sample may be prepared at one tilt angle, observed in a microscope, prepared again at a different tilt angle, and observed again. The ability to direct central beam axis 22 along more than one tilt angle allows for considerable refinement in sample preparation in the region of interest. Other aspects of the embodiments shown in FIG. 1 and FIG. 2 may be better understood now with reference to the following descriptions and figures.

Figure 3A:
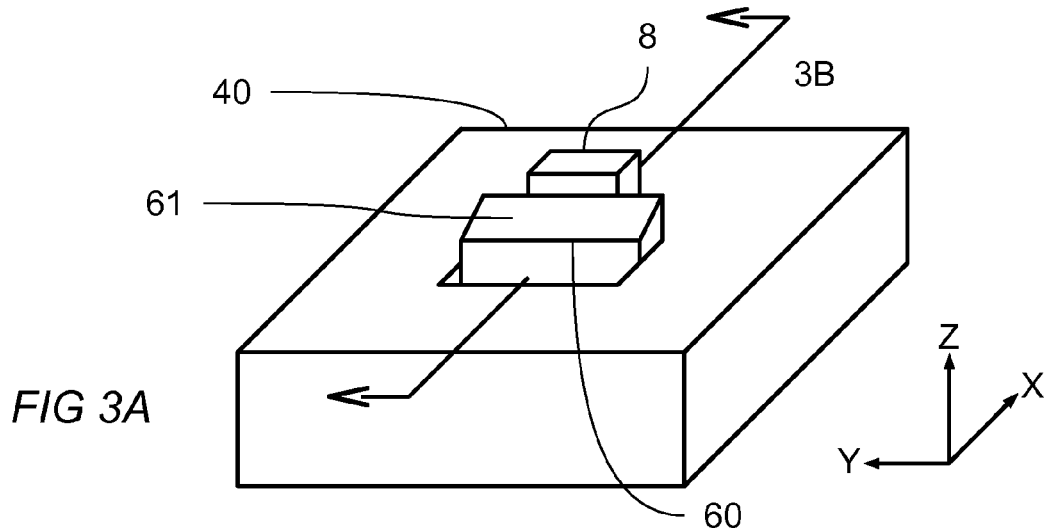
FIG. 3A shows a perspective view of a shield retention stage retaining a shield with a sample durably adhered to the shield. The figure also shows the cross section plane used for FIG. 3B.

FIG. 3A shows a perspective view of shield retention stage 40 on which sample 8 has been durably adhered to shield 60 prior to placing the shield and sample combination in a shield retaining position 46 in shield retention stage 40. Shield 60 has a shielding surface 61 which is positioned in relation to sample 8 to shield at least a portion of said sample 8 from at least a portion of the ion beam. Also shown in FIG. 3A is a section line indicating the section view shown in FIG. 3B.

Figure 3B:
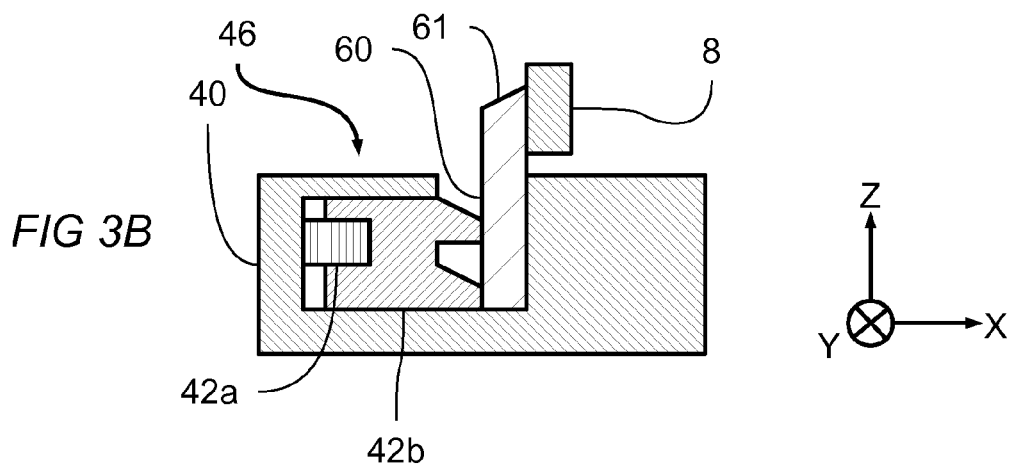
FIG. 3B shows a cross-sectional view of the shield retention stage of FIG. 3A with shield retention means in a shield retaining position.

FIG. 3B shows a section view illustrating the position and function of the shield retention means which is part of shield retention stage 40. FIG. 3B shows an embodiment of the shield retention means comprising a shield retention means first member 42a and a shield retention means second member 42b. Shield retention means first member 42a urges shield retention means second member 42b against shield 60. The action of shield retention means first member also urges shield 60 against shield retention stage 40, and thereby maintains the position of shield 60 within shield retention stage 40 while the sample is prepared by ion beam. An embodiment of the shield retention means may comprise a spring for shield retention means first member 42a and a solid member as shield retention means second member 42b configured to slide within a cavity in shield retention stage 40.

Figure 4:
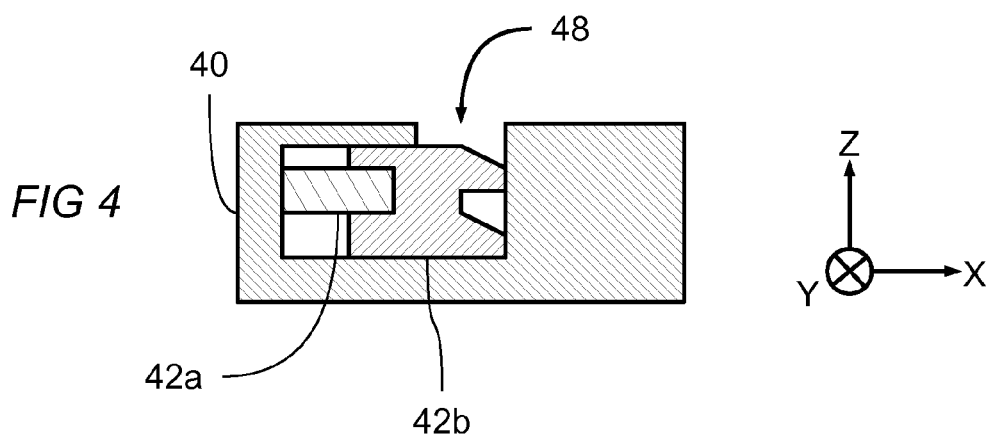
FIG. 4 shows a cross section similar to that of FIG. 3B, except that FIG. 4 shows the cross section with the shield retention means in a shield releasing position.

FIG. 4 shows a view from the same sectional plane as in FIG. 3B. However, in FIG. 4 the shield and sample have been removed to show a shield releasing position 48 of shield retention means. By means of the two positions provided by shield retention means, namely shield retaining position 46, as shown in FIG. 3A and FIG. 3B, and shield releasing position 48, as shown in FIG. 4, a shield may be removably and replaceably secured in shield retention stage 40. A sample that has been durably adhered to shield 60 may be processed, removed, and then reprocessed by simply placing it in the shield retaining position and preparing the sample again in the ion beam.

Figure 5A:
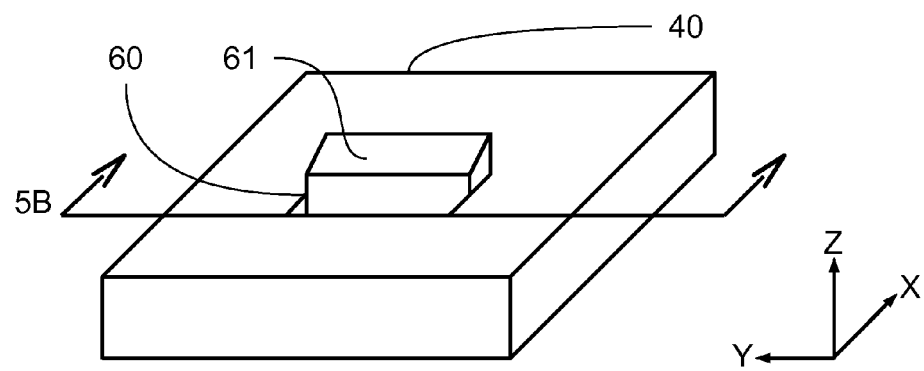
FIG. 5A shows a perspective view of a shield retention stage according to the present disclosure, indicating a cross-sectional plane for FIG. 5B.

FIG. 5A shows a perspective view of shield retention stage 40 on which shield 60 is retained, wherein said shield has a shielding surface 61. FIG. 5A also shows a sectional plane used for FIG. 5B.

Figure 5B:
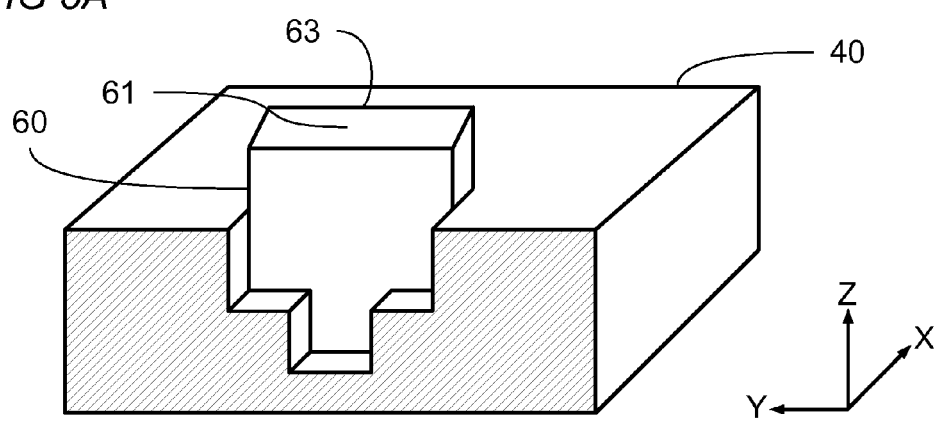
FIG. 5B shows a perspective sectional view of the shield retention stage of FIG. 5A, with the shield positioned in the shield retaining position.

FIG. 5B shows a sectional perspective view illustrating physical features of both shield 60 and shield retention stage 40 that facilitate accurate and repeatable positioning of the shield with respect to the shield retention stage. The positioning of shield 60 assures that shielding surface 61 and shield edge 63 are accurately positioned and accurately oriented with respect to the shield retention stage, and are positioned with respect to central ion beam axis 22 to intercept at least a portion of the ion beam directed toward the sample.

Figure 6:
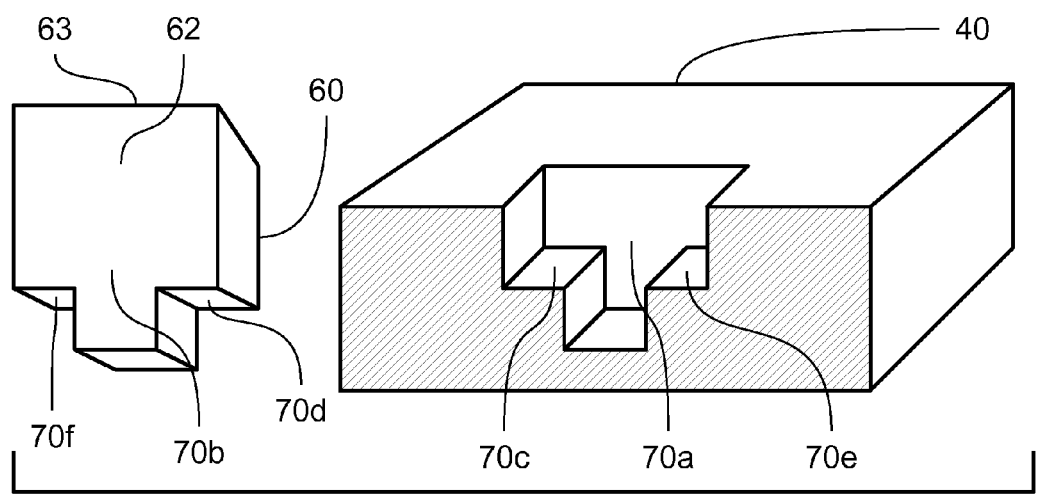
FIG. 6 shows an exploded perspective section view of the shield and shield retention stage of FIG. 5B. Datum features of both the shield and the shield retention stage are made visible in this view.

FIG. 6 shows a sectional perspective view as in FIG. 5B, in which preferred embodiments of both shield 60 and shield retention stage 40 have a plurality of datum features 70*a*, 70*b*, 70*c*, 70*d*, 70*e*, and 70*f*. In the exploded view shown in FIG. 6, shield 60 has been removed from shield retention stage 40 and the shield is turned to expose a proximal sample surface 62, upon which a sample may be durably adhered prior to sample preparation by the ion beam. The plurality of datum features 70*a*, 70*b*, 70*c*, 70*d*, 70*e*, and 70*f* is provided on both shield 60 and shield retention stage 40, and they enable accurate and repeatable positioning of the shield 60 with respect to the shield retention stage 40. Datum features 70*b*, 70*d*, and 70*f* on the shield are shaped and positioned such that when they are caused to abut complementary datum features 70*a*, 70*c*, and 70*e* on the shield retention stage, the shield may be held in a predetermined position and a predetermined orientation with respect to the central ion beam axis 22. Shield retention means 42 assures that datum features 70*b*, 70*d*, and 70*f* of shield 60 abut the corresponding datum features 70*a*, 70*c*, and 70*e* of the shield retention stage 40 when the shield is held in the shield retaining position. Shield edge 63, also visible in FIG. 6, is also caused to be in a predetermined position and predetermined orientation when the shield is held in the shield retaining position.

Datum features are arranged in pairs such that a datum feature on the shield has a corresponding datum feature on the shield retention stage. In FIG. 6, one such pair of datum features is datum feature 70*a* on the shield retention stage and datum feature 70*b* on the shield. Another pair of datum features shown in FIG. 6 is datum feature 70*c* on the shield retention stage and datum feature 70*d* on the shield. Another pair of datum features shown in FIG. 6 is datum feature 70*e* on the shield retention stage and datum feature 70*f* on the shield. When the shield is in the shield retaining position, the shield retention means acts to urge the pairs of datum features to abut, thereby constraining the position of the shield with respect to the position of the shield retention stage. Datum features may be datum surfaces, as is shown in the preferred embodiment of FIG. 6, or they may be datum edges or datum vertices, or combinations of datum surfaces, datum edges, and datum vertices.

Turning now to figures FIG. 7A, FIG. 7B, FIG. 8A, FIG. 8B, FIG. 9, and FIG. 10, shown are various features and embodiments of shield 60 according to the present disclosure.

Figure 7A:
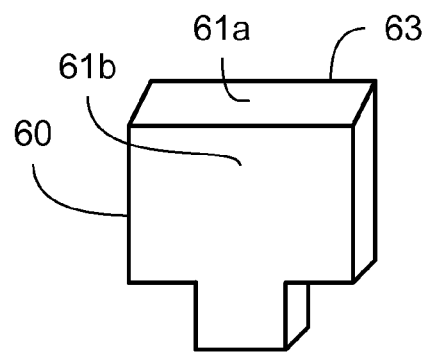
FIGS. 7A and 7B show perspective views of a shield according to embodiments of the present disclosure, viewed from the ion beam side of the shield.
Figure 15A:
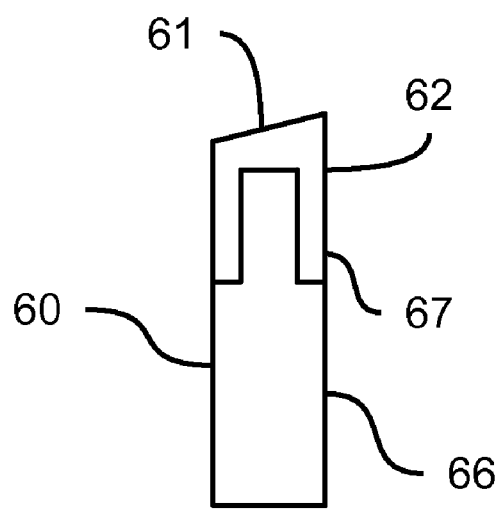
FIG. 15A and FIG. 15B show schematic views of embodiments of a shield comprising core material and cladding material.
Figure 15B:
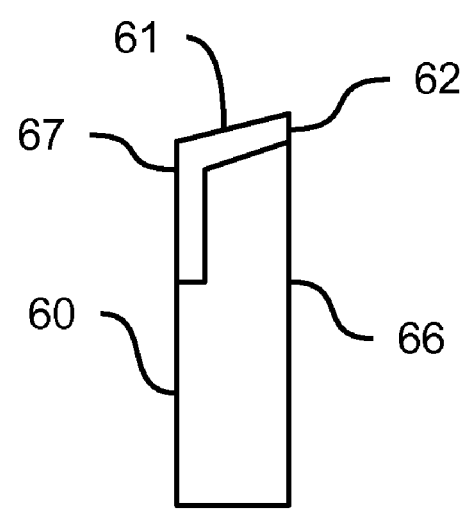

FIG. 7A is a perspective view of a shield showing a first shielding surface 61*a*, a second shielding surface 61*b*, and shield edge 63. Ions from the ion beam irradiating means that are blocked by the shield, and, in particular, the ions that are blocked by first shielding surface 61*a*, are prevented from milling the sample. Ions not blocked by the shield may be used to prepare the sample for observation and analysis. When the ion beam is operating, ions may or may not impact second shielding surface 61*b*. Whether ions do impact second shielding surface 61*b* depends on a number a factors including, but not limited to: the size of the ion beam; the angle at which the ion beam is directed; and, the position at which the ion beam is directed. It is a preferred embodiment of the shield that second shielding surface 61*b* be made of the same material as first shielding surface 61*a*. In preferred embodiments, shield 60 is a generally planar rigid member, having one or more shielding surfaces that are smooth and may be polished, having a datum surface and at least an additional datum feature for facilitating accurate placement within the shield retention stage. Preferred materials for the shield are non-magnetic metals with low sputtering-yield including, but not limited to, tantalum or titanium. Lower cost embodiments of shield 60 may comprise core material 66 for the majority of the shield and cladding material 67 used for the shielding surfaces. Preferred core materials include, but are not limited to, copper. Preferred cladding materials include, but are not limited to, tantalum or titanium. Figures FIG. 15A and FIG. 15B illustrate two different embodiments of a shield 60, wherein each embodiment is shown comprising a combination of core material 66 and cladding material 67.

Figure 7B:
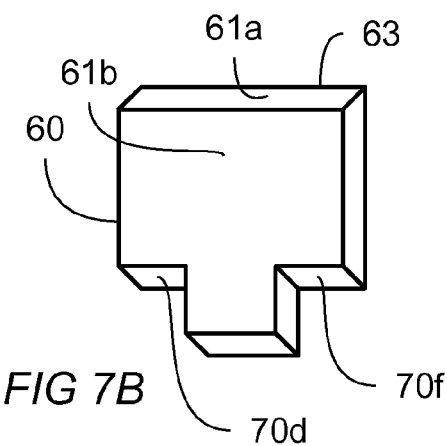

FIG. 7B shows the same shield as shown in FIG. 7A, but from a different angle thereby illustrating the position and nature of a plurality of datum features 70*d* and 70*f*.

Figure 8A:
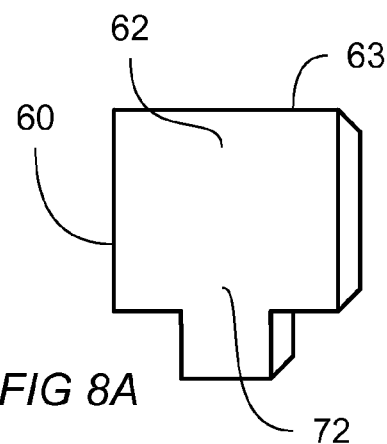
FIGS. 8A and 8B show perspective views of a shield according to embodiments of the present disclosure, viewed from the proximal sample side of the shield.

FIG. 8A shows the same shield as shown in FIG. 7A and FIG. 7B. FIG. 8A shows a perspective view of shield 60 from the side of the shield closest to the sample during ion beam sample preparation. Proximal sample surface 62 may be used to adhere the sample material to be prepared in the apparatus. Datum surface 72 is a datum feature that is a surface. In a preferred embodiment, at least a portion of proximal sample surface 62 may be coextensive with at least a portion of datum surface 72. Shield edge 63 is formed by the intersection of first shielding surface 61*a* and proximal sample surface 62. The angle between first shielding surface 61*a* and proximal sample surface 62 has an impact on the quality of milling performed on the sample by the ion beam. A preferred embodiment is achieved when said first shielding surface 61*a* meets said proximal sample surface 62 at an angle of less than about 90 degrees and more than about 80 degrees. An even more preferred embodiment is achieved when said first shielding surface 61*a* meets said proximal sample surface 62 at an angle of less than about 87 degrees and more than about 83 degrees.

Figure 8B:
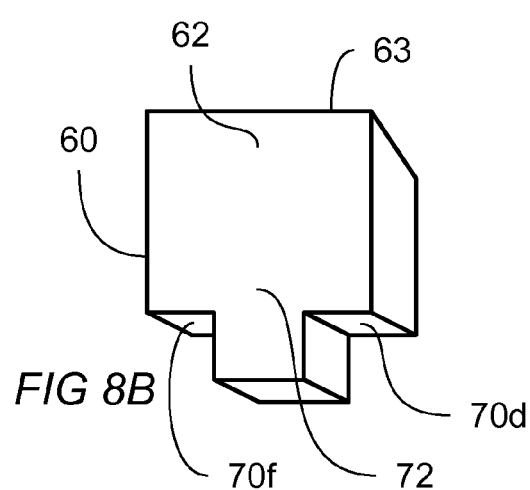

FIG. 8B shows the same shield as shown in FIG. 8A, but from a different angle thereby illustrating the position and nature of a plurality of datum features 70*d* and 70*f*, and datum surface 72, present on shield 60.

Figure 9:
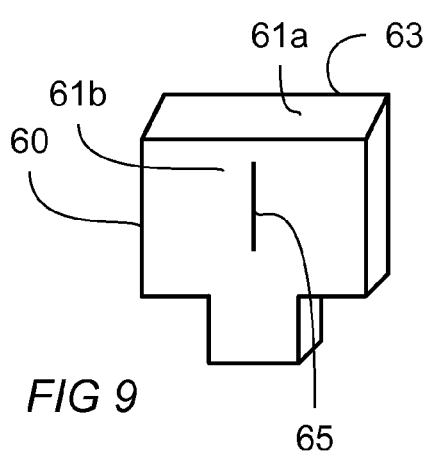
FIG. 9 shows a perspective view of another shield according to the present disclosure, viewed from the ion beam side of the shield and having a visible alignment feature.

FIG. 9 shows a perspective view of shield 60, having first shielding surface 61*a*, second shielding surface 61*b*, shield edge 63, and additionally comprising a visible alignment mark 65. When the shield is held in the shield retaining position, the visible alignment mark is positioned so that it indicates the approximate location where a portion of the ion beam will pass over shield edge 63 and impact the sample when the shield edge is substantially perpendicular to the central ion beam axis.

Figure 10:
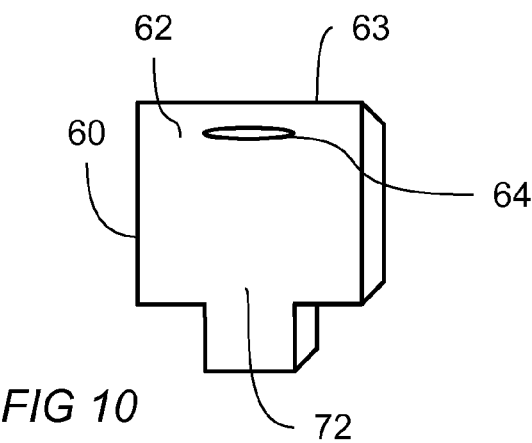
FIG. 10 shows a perspective view of another shield according to the present disclosure, viewed from the proximal sample side of the shield and having a recessed portion to facilitate the flow of adhesive under the sample.

FIG. 10 shows a perspective view of shield 60 from the side of the shield closest to the sample during ion beam sample preparation. Proximal sample surface 62 may be used to adhere the sample material to the shield prior to ion beam sample preparation in the apparatus. Recessed portion 64 provides a recessed portion of proximal sample surface 62 useful for flowing adhesive under the sample, thereby facilitating the durable adhering of sample to shield. Preferred materials used to adhere the sample to the shield include, but are not limited to: UV cured glue, light cured glue, superglue, silver paint, and wax.

Turning now to FIG. 11A, shown is a perspective view of shield 60, shielding surface 61, sample 8 durably adhered to the shield, and visible alignment mark 65. FIG. 11A depicts the sample prior to ion beam preparation. FIG. 11B is a perspective view of the same objects depicted in FIG. 11A. However, FIG. 11B represents the sample after ion beam sample preparation. Shielding surface 61 intercepts a portion of the ion beam, which travels along central ion beam axis 22. A portion of sample 8 is sputtered away by the ion beam during sample preparation, thereby exposing a portion of the sample lying in the plane defined by shield edge 63 and central ion beam axis 22. A sample prepared in this way will be suitable for observation or analysis with a variety of microscopic or spectroscopic techniques, particularly those requiring a highly polished planar surface.

FIGS. 12A and 12B illustrate another embodiment of shield 60, in which a sample clamping means 68 is formed integrally with the shield on the proximal sample surface 62. FIG. 12A depicts this shield prior to clamping a sample, while FIG. 12B depicts this shield after sample 8 has been secured to the shield by means of sample clamping means 68. In another embodiment, sample clamping means 68 may be formed separately, and then coupled to the shield prior to clamping the sample. Adhesive may be applied between the sample clamping means and the sample to further ensure the sample does not move with respect to the shield.

Use of the apparatus shown in FIG. 1 may proceed with reference to the following steps: outside of the vacuum chamber, a sample may be durably adhered to a shield; with the chamber cover removed, the sample and shield combination may be set in the shield retaining position of the shield retention stage; the chamber cover may then be replaced; with the chamber cover in place on the vacuum chamber, the vacuum pump means may be operated to evacuate the vacuum chamber through the pumping manifold, thereby obtaining vacuum levels appropriate for ion beam milling; the ion beam irradiating means may then be operated to prepare the sample. When the sample is prepared to the extent desired by the user of the apparatus, the ion beam irradiating means may be turned off, the vacuum chamber may be returned to atmospheric conditions, the chamber cover may be removed, and the prepared sample may be removed from the apparatus along with the shield to which it was previously adhered. A microscope may be fitted with a shield retention stage so that the prepared sample and shield may be retained, and thereby the prepared region of the sample may be observed in the microscope. After observation the user may decide that additional sample preparation is needed. Since the sample is still durably adhered to the shield, it is a simple matter to return the sample and shield to the vacuum chamber for additional processing. The datum features on both the shield and the shield retention stage ensure that the shield may be retained in substantially the same position and orientation each time the sample is processed in the apparatus. A kit comprising a shield retention stage 40 with a plurality of datum features 70a, 70c, and 70e, shield retention means 42, and at least one shield 60 with a plurality of datum features 70b, 70d, and 70f may be supplied for fitting to a microscope. Such a kit facilitates the microscopic observation of samples prepared in the ion beam sample preparation apparatus 2.

Figure 13A:
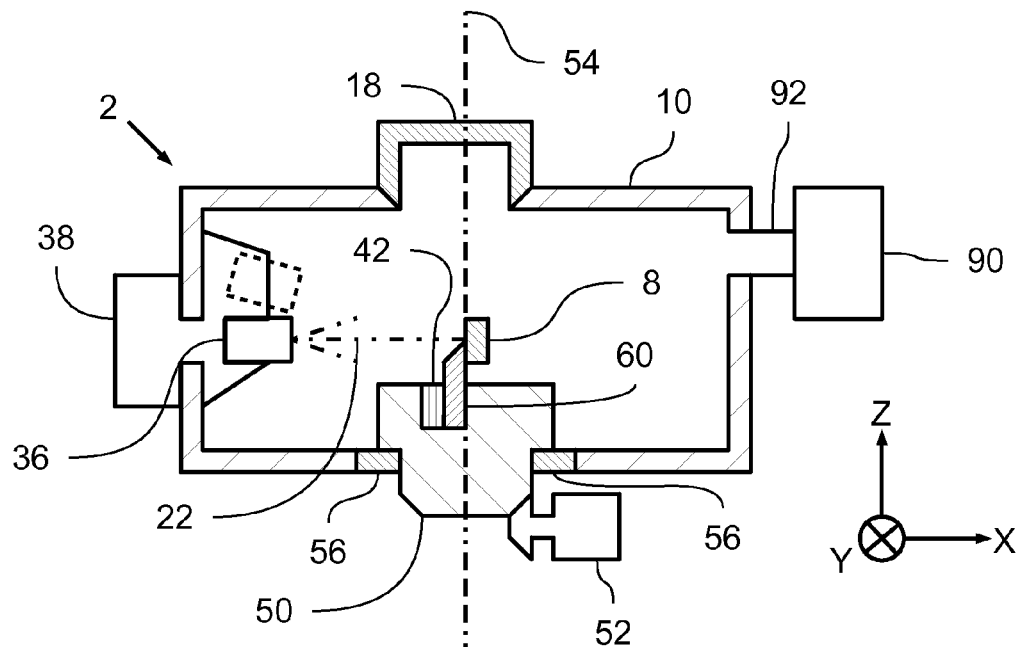
FIG. 13A shows a schematic cross sectional view of an ion beam sample preparation apparatus according to an embodiment of the disclosure featuring tilting ion beam irradiating means and a rotating shield retention stage. The tilting irradiating ion beam means is shown with the tilting ion beam irradiating means at a first tilt angle.
Figure 13B:
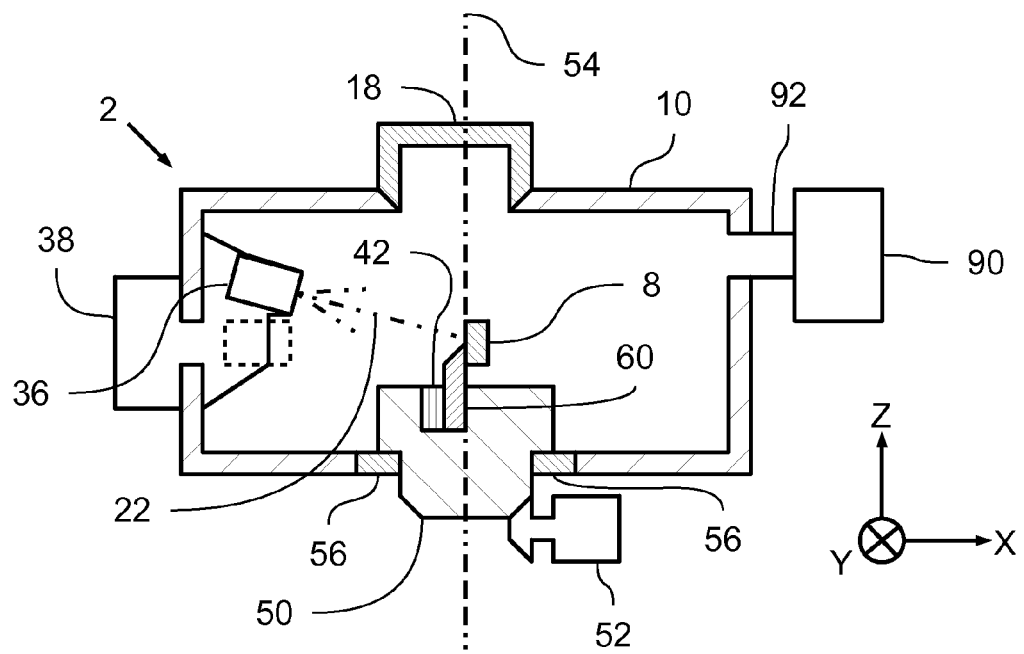
FIG. 13B shows a schematic cross sectional view of the apparatus of FIG. 13A at a second tilt angle.

Turning now to FIG. 13A and FIG. 13B, shown are another embodiment of an ion beam sample preparation apparatus according to the present disclosure. The embodiment of FIG. 13A and FIG. 13B comprises: a vacuum chamber 10 in which a sample 8 is prepared; chamber cover 18 which seals vacuum chamber 10 from the outside atmosphere; vacuum pump means 90, and pumping manifold 92 which together bring vacuum chamber 10 to vacuum levels appropriate for ion beam milling; tilting ion beam irradiating means 36 and tilt drive 38, which direct an ion beam having a central ion beam axis 22 toward sample 8; a shield 60, which shields at least a portion of sample 8 from at least a portion of the ion beam; a rotating shield retention stage 50, which holds and accurately positions shield 60 with respect to the direction and extent of the ion beam; a shield retention means 42, which both retains shield 60 in rotating shield retention stage 50 and also urges shield 60 to remain in a position whereby the ion beam may prepare sample 8; a rotation drive 52, which rotates the rotating shield retention stage 50 about rotation axis 54; and vacuum seal 56, which maintains the vacuum in vacuum chamber 10, while allowing rotating shield retention stage 50 to move about rotation axis 54. In preferred embodiment, rotation axis 54 lies substantially in the plane defined by the abutment of the proximal sample surface 62 with the sample 8. Shield 60 of figures FIG. 13A and FIG. 13B has the same features, functions, and aspects possessed by shield 60 shown in figures FIG. 3A, FIG. 3B, FIG. 5A, FIG. 5B, FIG. 6, FIG. 7A, FIG. 7B, FIG. 8A, and FIG. 8B.

With continuing reference to FIG. 13A and FIG. 13B, the ion beam preferably comprises noble gas ions. Elements used for the ion beam may include but are not limited to: argon, xenon, and krypton. The ion beam may also comprise a mixture of ions and neutrals. Shield retention stage 50 is disposed in vacuum chamber 10 in a predetermined position and orientation with respect to central beam axis 22. Rotating shield retention stage 50 may additionally comprise means for measuring the rotation angle of the stage. Rotation drive 52 may additionally comprise means to reach and maintain accurate angular position. Rotation drive 52 may additionally comprise means to reach and maintain accurate angular speed. Rotation drive 52 enables rotating shield retention stage 50 to rotate about rotation axis 54. In a preferred embodiment, shield edge 63 is disposed substantially perpendicular to rotation axis 54 when shield 60 is held in the shield retaining position.

In the apparatus of FIG. 13A and FIG. 13B, tilting ion beam irradiating means 36 and tilt drive 38 enable the ion beam to prepare the sample by directing central ion beam axis 22 toward sample 8 from more than one angle. FIG. 13A shows tilting ion beam irradiating means 36 at a first angle, while FIG. 13B shows tilting ion beam irradiating means 36 at a second angle. In a preferred embodiment, tilting ion beam irradiating means 36 and tilt drive 38 are adapted to provide a variable degree of tilt angle while maintaining central ion beam axis 22 substantially perpendicular to shield edge 63 for at least a portion of tilt angle. In a preferred embodiment, tilting ion beam irradiating means 36 and tilt drive 38 are adapted to provide a variable degree of tilt angle while central ion beam axis 22 substantially intersects rotation axis 54 for at least a portion of tilt angle.

Figure 14A:
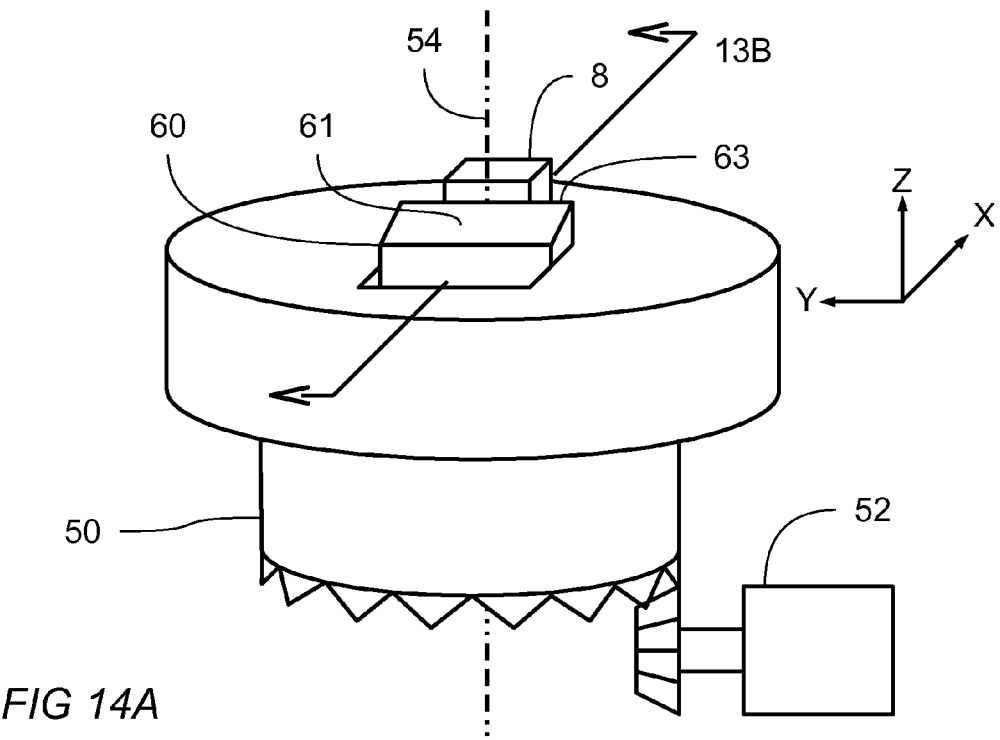
FIG. 14A shows a schematic perspective view of a rotating shield retention stage and rotation drive according to embodiments of the present disclosure.
Figure 14B:
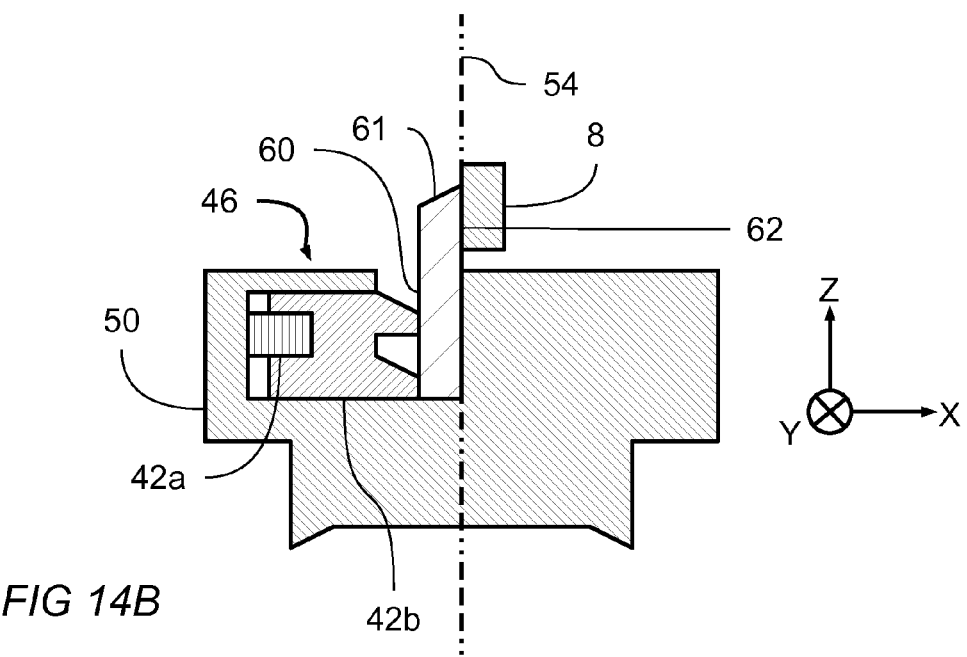
FIG. 14B shows a cross-sectional view of the rotating shield retention stage of FIG. 14A with shield retention means in a shield retaining position.

Features and aspects of rotating shield retention stage 50 may be better understood now with reference to FIG. 14A and FIG. 14B and the written description that follows.

FIG. 14A shows a perspective schematic view of rotating shield retention stage 50, on which sample 8 has been durably adhered to shield 60 prior to placing the shield and sample combination in a shield retaining position of rotating shield retention stage 50. Shield 60 has a shielding surface 61, which is positioned in relation to sample 8 to shield at least a portion of said sample 8 from at least a portion of the ion beam. Rotation drive 52 enables rotating shield retention stage 50 to rotate about rotation axis 54. In a preferred embodiment, shield edge 63 is disposed to be substantially perpendicular to rotation axis 54 when shield 60 is held in the shield retaining position. Also shown in FIG. 14A is a section line indicating the section view shown in FIG. 14B.

FIG. 14B shows a section view illustrating the position and function of the shield retention means, which is part of rotating shield retention stage 50. In FIG. 14B shield retention means first member 42a urges shield retention means second member 42b against shield 60. The action of shield retention means first member 42a also urges shield 60 against rotating shield retention stage 50 and thereby maintains the position of shield 60 within rotating shield retention stage 50 while the sample is prepared by the ion beam. An embodiment of the shield retention means may comprise a spring for shield retention means first member 42a and a solid member as shield retention means second member 42b configured to slide within a cavity in rotating shield retention stage 50. The shield retention means also has a shield releasing position in which the shield and sample are not held in the rotating shield retention stage 50. The shield releasing position may be identical to the shield releasing position 48 illustrated in FIG. 4. In a preferred embodiment, rotation axis 54 lies substantially in the plane defined by the abutment of the proximal sample surface 62 with the sample 8.

The rotating shield retention stage 50 has the same plurality of datum features as shown on the non-rotating shield retention stage of FIG. 6. In addition, the rotating shield retention stage 50 datum features allow the interchangeable use of shield 60 previously described. The datum features of the shield retention stage 40 and the rotating shield retention stage 50 are substantially identical in design, and thereby facilitate the easy interchange of shields between the stages. By means of the two positions provided by the shield retention means, namely shield retaining position 46, as shown in FIG. 3B, and shield releasing position 48, as shown in FIG. 4, a shield may be removably and replaceably secured in rotating shield retention stage 50. A sample that has been durably adhered to shield 60 may be processed, removed, and then reprocessed by simply placing it in the shield retaining position and preparing the sample again in the ion beam. The datum features on both shield and shield retention stage assure that the shield may be positioned in a substantially identical position and orientation multiple times. In preferred embodiments that include rotating shield retention stage 50, central ion beam axis 22 passes substantially through rotation axis 54 in the region above shield edge 63. After the sample has been prepared by the ion beam in the vacuum chamber, chamber cover 18 may be removed, and then the shield and sample may be removed for observation in a microscope.

Use of the apparatus of figures FIG. 13A and FIG. 13B may proceed according to all of the steps disclosed for the use of the apparatus of FIG. 1 and FIG. 2. However, the rotating shield retention stage FIG. 13A and FIG. 13B gives the user additional capabilities. In particular, the use of the rotating shield retention stage during sample preparation may improve the evenness of the prepared region if that region of the sample has local variations in physical consistency that lead to different rates of preparation by the ion beam. Rotation during sample preparation may have a beneficial leveling effect on such a sample. In addition, the user may rotate the rotating shield retention stage about the rotation axis to a desired angle before sample preparation, during sample preparation, or after sample preparation. Also, the rotation drive and the tilt drive may operate in concert to accurately and repeatably control the ion beam tilt as a function of the rotation angle of the rotating shield retention stage. Thus, the user has increased flexibility in exposing and preparing a region of interest in the sample for later microscopic observation.

With continuing reference to FIG. 13A and FIG. 13B, the ion beam preferably comprises noble gas ions. Elements used for the ion beam may include but are not limited to: argon, xenon, and krypton. The ion beam may also comprise a mixture of ions and neutrals. Rotating shield retention stage 50 is disposed in vacuum chamber 10 in a predetermined position and orientation with respect to central ion beam axis 22. Rotating shield retention stage 50 may additionally comprise means for measuring the rotation angle of the stage. Rotation drive 52 may additionally comprise means to reach and maintain accurate angular position. Rotation drive 52 may additionally comprise means to reach and maintain accurate angular speed. In addition, shield 60 of FIG. 13A and FIG. 13B has the same features, functions, and aspects possessed by shield 60 shown in figures FIG. 3A, FIG. 3B, FIG. 5A, FIG. 5B, FIG. 6, FIG. 7A, FIG. 7B, FIG. 8A, FIG. 8B, FIG. 14A, and FIG. 14B. In a preferred embodiment, as shown in FIG. 14A and FIG. 14B, rotation axis 54 lies substantially in the plane defined by the abutment of the proximal sample surface 62 with the sample 8.

Although the present invention has been described in considerable detail with reference to certain preferred versions thereof, other versions are possible. For example, it may be desirable to combine features shown in various embodiments into a single embodiment. For example, materials or alloys that are both non-magnetic and have low sputtering-yield may be used with success for shielding surfaces and may be constructed and used entirely within the spirit and scope of the present disclosure. Therefore, the spirit and scope of the appended claims should not be limited to the description of the preferred versions contained herein.

Any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" in the claims herein is not intended to invoke the provisions of 35 U.S.C. Section 112, Paragraph 6.

The invention claimed is:

1. An ion beam sample preparation apparatus comprising:
   a) a tilting ion beam irradiating means disposed in a vacuum chamber and directing an ion beam toward a shield, characterized in that said tilting ion beam irradiating means projects an ion beam along a central ion beam axis, the direction of said central ion beam axis having a tilt angle with respect to said shield;
   b) a tilt drive operably coupled to said tilting ion beam irradiating means and configured to move the direction of said central ion beam axis between at least two different tilt angles;
   c) a shield retention stage disposed in the vacuum chamber; said shield retention stage comprising:
      i) a first datum feature;
      ii) a second datum feature;
      iii) a shield retention means having at least a shield releasing position and a shield retaining position;
   d) the shield having at least a rigid planar portion, removably and replaceably held in said shield retention stage, said shield further comprising:
      i) a proximal sample surface configured to durably adhere the sample to the shield;
      ii) a first shielding surface disposed in the path of the ion beam and positioned to shield a portion of the ion beam directed at the sample when said shield is held in the shield retaining position of the shield retention means;
      iii) a third datum feature formed integrally with said shield, wherein said shield retention means in said shield retaining position urges said third datum feature to abut said first datum feature; and,
      iv) a fourth datum feature formed integrally with said shield, wherein said shield retention means in said shield retaining position urges said fourth datum feature to abut said second datum feature.

2. The apparatus of claim 1 wherein the shield retention stage further comprises a fifth datum feature, and the shield further comprises a sixth datum feature formed integrally with the shield, wherein the shield retention means in said shield retaining position urges said sixth datum feature to abut said fifth datum feature.

3. The apparatus of claim 1 wherein the first shielding surface meets said proximal sample surface at an angle of less than about 90 degrees and more than about 80 degrees.

4. The apparatus of claim 1 wherein the first shielding surface meets said proximal sample surface at an angle of less than about 87 degrees and more than about 83 degrees.

5. The apparatus of claim 1 wherein the first shielding surface is made of non-magnetic material having low sputtering-yield.

6. The apparatus of claim 1 wherein at least a portion of the first shielding surface is made of tantalum or titanium.

7. The apparatus of claim 1 wherein the third datum feature is a datum surface and at least a portion of said datum surface is coextensive with at least a portion of said proximal sample surface.

8. The apparatus of claim 1 wherein the proximal sample surface has at least one recessed portion configured for the flowing of adhesive between the shield and the sample.

9. The apparatus of claim 1 wherein the shield further comprises a sample clamping means coupled to the shield and configured to hold the sample against said proximal sample surface.

10. The apparatus of claim 1 wherein the shield further comprises:
   a) a second shielding surface having a portion disposed in the path of a portion of the ion beam;
   b) a shield edge formed where the first shielding surface meets the proximal sample surface; and,
   c) a visible alignment mark on the second shielding surface, configured such that the location of said visible alignment mark is in a predetermined relationship to the region where the ion beam impinges on said shield edge when said shield is held in the shield retaining position of the shield retention means.

11. The apparatus of claim 1 wherein the shield is made of a cladding material joined to a core material such that a portion of the cladding material forms at least a portion of the first shielding surface, and a portion of the core material forms said third datum feature of the shield and said fourth datum feature of the shield.

12. The apparatus of claim 11 wherein the cladding material is a non-magnetic material having low sputtering-yield.

13. An ion beam sample preparation apparatus comprising:
   a) a tilting ion beam irradiating means disposed in a vacuum chamber and directing an ion beam toward a shield, characterized in that said tilting ion beam irradiating means projects an ion beam along a central ion beam axis, the direction of said central ion beam axis having a tilt angle with respect to said shield;
   b) a tilt drive operably coupled to said tilting ion beam irradiating means and configured to move the direction of said central ion beam axis between at least two different tilt angles;
   c) a rotating shield retention stage disposed in the vacuum chamber; said rotating shield retention stage comprising:
      i) a first datum feature;
      ii) a second datum feature;
      iii) a shield retention means having at least a shield releasing position and a shield retaining position;
      iv) a rotation axis located substantially in the plane of the first datum feature;
      v) a rotation drive for rotating the rotating shield retention stage around the rotation axis;
   d) the shield having at least a rigid planar portion, removably and replaceably held in said rotating shield retention stage, said shield further comprising:
      i) a third datum feature formed integrally with the shield, wherein said shield retention means in said shield retaining position urges said third datum feature to abut said first datum feature;
      ii) a fourth datum feature formed integrally with the shield, wherein said shield retention means in said shield retaining position urges said fourth datum feature to abut said second datum feature;
      iii) a first shielding surface disposed in the path of the ion beam and positioned to shield a portion of the ion beam directed at the sample when said shield is held in the shield retaining position of the shield retention means;
      iv) a proximal sample surface configured to durably adhere the sample to the shield;
      v) a shield edge formed where the first shielding surface meets the proximal sample surface, characterized in that said shield edge is held substantially perpendicular to said rotation axis when said shield is held in the shield retaining position of the shield retention means.

14. The apparatus of claim 13 further characterized in that the tilting ion beam irradiating means and tilt drive are adapted to provide at least two different tilt angles in which the central ion beam axis is substantially perpendicular to said shield edge.

15. The apparatus of claim 13 further characterized in that the tilting ion beam irradiating means and tilt drive are adapted to provide at least two different tilt angles in which the central ion beam axis substantially intersects said rotation axis.

16. The apparatus of claim 13 wherein the rotating shield retention stage further comprises a fifth datum feature, and the shield further comprises a sixth datum feature formed integrally with the shield, wherein the shield retention means in said shield retaining position urges said sixth datum feature to abut said fifth datum feature.

17. The apparatus of claim 13 wherein the first shielding surface meets said proximal sample surface at an angle of less than about 90 degrees and more than about 80 degrees.

18. The apparatus of claim 13 wherein the first shielding surface meets said proximal sample surface at an angle of less than about 87 degrees and more than about 83 degrees.

19. The apparatus of claim 13 wherein the first shielding surface is made of non-magnetic material with low sputtering-yield.

20. The apparatus of claim 13 wherein at least a portion of the first shielding surface is made of tantalum or titanium.

21. The apparatus of claim 13 wherein the third datum feature is a datum surface and a portion of said datum surface is coextensive with a portion of said proximal sample surface.

22. The apparatus of claim 13 wherein the proximal sample surface has at least one recessed portion configured for the flowing of adhesive between the shield and the sample.

23. The apparatus of claim 13 wherein the shield further comprises a sample clamping means coupled to the shield and configured to hold the sample against said proximal sample surface.

24. The apparatus of claim 13 wherein the shield further comprises:
   a) a second shielding surface having a portion disposed in the path of a portion of the ion beam;
   b) a visible alignment mark on the second shielding surface, configured such that the location of said visible alignment mark is in a predetermined relationship to the region where the ion beam impinges on said shield edge when said shield is held in the shield retaining position of the shield retention means.

25. The apparatus of claim 13 wherein the shield is made of a cladding material joined to a core material such that a portion of the cladding material forms at least a portion of the first shielding surface, and a portion of the core material forms the third and fourth datum features of the shield.

26. The apparatus of claim 25 wherein the cladding material is a non-magnetic material having low sputtering-yield.

* * * * *